United States Patent [19]

Deitch

[11] Patent Number: 4,483,336

[45] Date of Patent: Nov. 20, 1984

[54] UNIVERSAL SUSPENSORY LEG CAST AND SPLINT SUPPORT

[76] Inventor: Earl W. Deitch, 5606 Browne St., Omaha, Nebr. 68104

[21] Appl. No.: 160,142

[22] Filed: Jun. 16, 1980

[51] Int. Cl.³ .............................................. A61F 5/40
[52] U.S. Cl. ......................................... 128/94; 2/310
[58] Field of Search ................. 2/310; 128/94, 85, 83, 128/83.5, 80 G

[56] References Cited

U.S. PATENT DOCUMENTS

| | | | |
|---|---|---|---|
| 776,908 | 12/1904 | Henry | 128/94 UX |
| 1,860,727 | 5/1932 | Ansley | 2/310 X |
| 2,543,847 | 3/1951 | Hallstedt | 128/94 |
| 3,739,772 | 6/1973 | Ennis | 128/80 G |
| 4,188,944 | 2/1980 | Augustyniak | 128/94 |
| 4,198,964 | 4/1980 | Honneffer | 128/94 X |

Primary Examiner—H. Hampton Hunter
Attorney, Agent, or Firm—Zarley, McKee, Thomte, Voorhees & Sease

[57] ABSTRACT

An over-the-shoulder suspensory support device for use with leg casts, leg splints, and amputation casts is disclosed. The device provides a comfortable, adjustable, resilient support strap, an adjustable, removable positioning strap and co-acting tabs for use with casts and splints. A method for using the support device is also disclosed.

3 Claims, 8 Drawing Figures

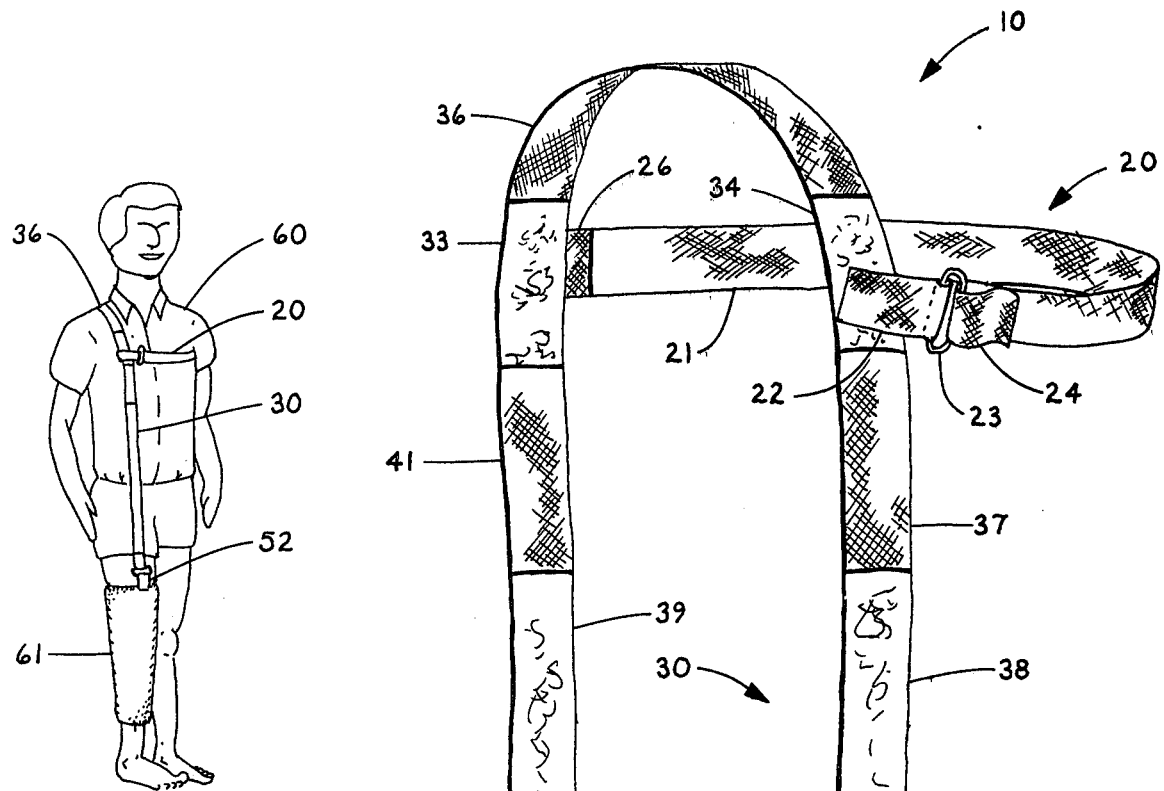
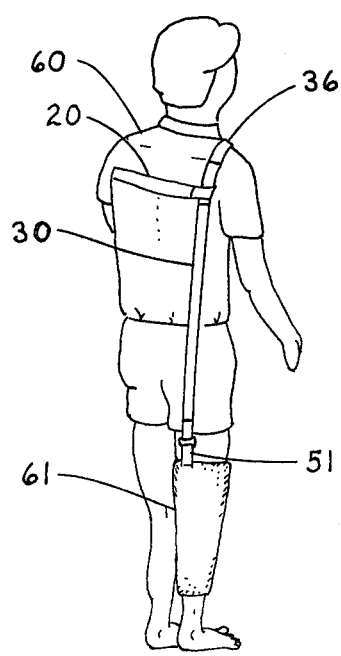
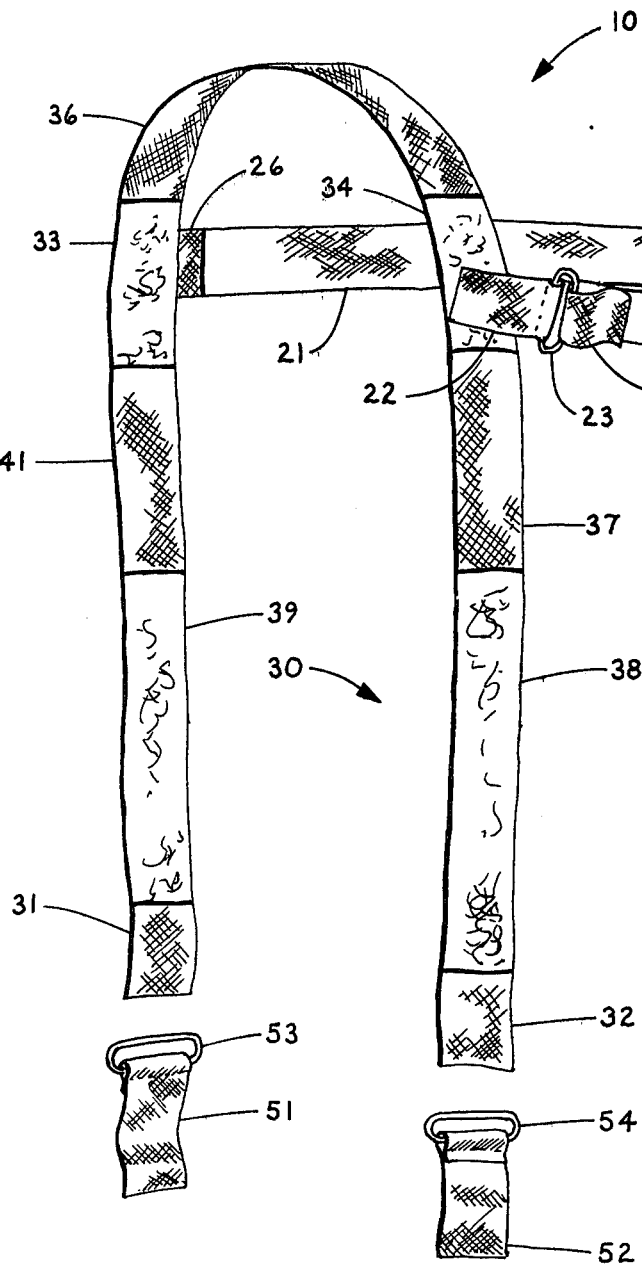
fig. 1
fig. 2
fig. 3

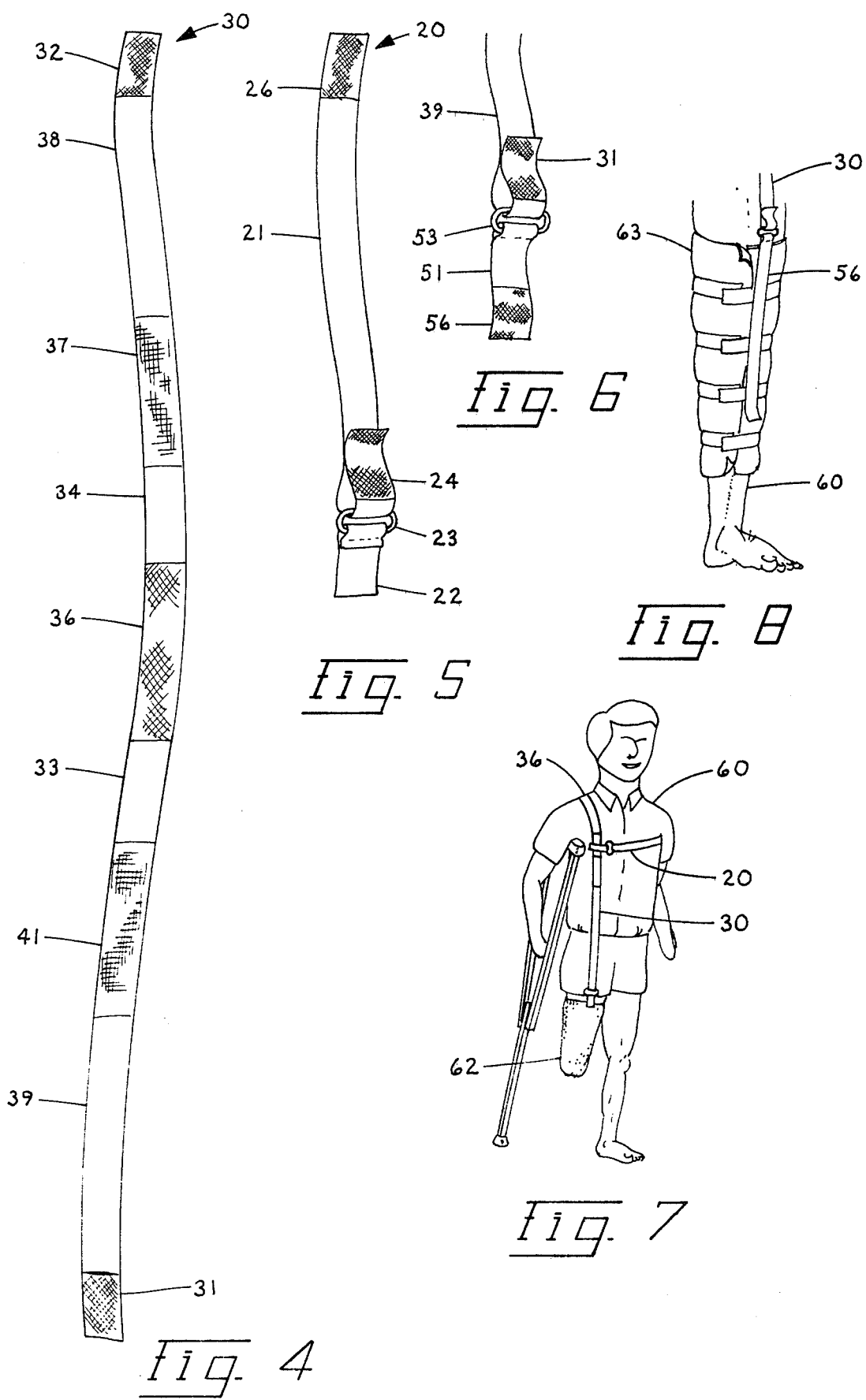

UNIVERSAL SUSPENSORY LEG CAST AND SPLINT SUPPORT

BACKGROUND OF THE INVENTION

1. Field of the Invention

This invention relates generally to support devices for use with leg casts, leg splints and amputation casts, and particularly to an over-the-shoulder suspensory support which is universal and adjustable.

2. Description of the Prior Art

The state of the prior art as disclosed in issued patents known to the applicant includes U.S. Pat. No. 2,543,847 to Hallstedt, which is a sling for the use in the treatment of certain leg diseases, and U.S. Pat. No. 3,739,772 to Ennis, which provides a resilient harness device for a walking cast. Both the Hallstedt and Ennis patents involve cross shoulder slings. The Hallstedt sling is for use with a leg in a bent position and the Ennis harness provides a foot band to be used with a walking cast.

The prior art discloses use of leg casts for leg and knee injuries. In some cases, the entire leg, including the foot is included in the cast. In other instances, a cylindrical cast, extending from the groin to the ankle, not including the foot, is used. This shortened case is applied for various types of knee problems in which a greater amount of support is required for the knee than is available through a splint. Commonly, the cylindrical cast is used for fractures of the patella. Due to the shape of the leg, the cylindrical cast tends to slide down and puts pressure on both the ankle and the top of the foot.

Of course, one may limit the slippage of the cast by enclosing the foot with the cast, so that the entire leg is immobilized. A walking cast of that type is shown in Ennis U.S. Pat. No. 3,739,772. Unfortunately, the walking cast is uncomfortable compared to a cylindrical cast which leaves the foot out of the plaster.

A cylindrical cast which does not enclose the foot and ankle allows the patient to wear a regular shoe. Nevertheless, the problem remains of the cast tending to slide down which abrades the leg and places pressure on both the ankle and the top of the foot.

The long leg cast which includes the foot is used in many types of lower extremity injuries. The injuries include ligament injuries of the knee and most types of fractures, such as tibial and fibula shaft fractures. As previously mentioned, in some instances, the long leg cast can be an ambulatory cast, or walking cast, and includes a rubber walking heel.

A suspensory strap is generally not required with a walking cast; however, if the injury or the fracture is of such a nature that weight bearing is not advisable, the cast must be supported on the dorsal surface of the foot which causes discomfort. A web strap incorporated into a cast and buckled to a pelvic band or waist strap has been used in order to decrease the weight of the cast upon the leg.

A third type of cast known as a cast brace is also used. A cast brace is a type of cast which includes a plaster thigh portion, a plaster short leg portion below the knee including the foot and metal or plastic hinges joining the two plaster portions. The cast brace is often made of synthetic material such as fiberglass. The cast brace is used for the treatment of femoral shaft fractures and various types of tibial plateau fractures. The cast brace also has a tendency to slip when being worn.

In the technique of immediate post-surgical fitting or prostheses following amputations, a plaster cast is applied over the amputation stump with a pylon and a prosthetic foot. The cast is usually suspended from a pelvic strap. Around-the-neck and pelvic straps are shown and described on pages 885 through 896 from *Campbell's Operative Orthopaedics*. Unfortunately, many of the straps and devices are extremely complex and require having a prosthetist in the operating room.

Accordingly, there exists a need for a cast and splint support device which is universal, so that it can be used with different casts and splints, that is adjustable, resilient, and inexpensive. Applicant's invention is directed toward that need. Applicant's invention provides an easily ajustable multi-purpose over-the-shoulder suspensory support for the use with leg casts, leg splints and amputation casts.

SUMMARY OF THE INVENTION

The present invention is directed toward overcoming the disadvantages and problems relative to walking cast harnesses, pelvic straps, pelvic suspensory straps and complex around-the-neck and over-the-shoulder suspensory straps. An important feature of the present invention is its universal applicability to casts of all types and descriptions, splints, cast braces and amputation casts. The present invention, thus, eliminates the necessity for particularized support devices and limits the inventory that an orthopaedic surgeon must maintain to fit his patients.

One of the principal objects of the present invention is to provide an over-the-shoulder suspensory support device for use with leg casts, leg splints, and amputation casts which may be used for a wide range of different size persons, and yet firmly, securely and resiliently provides support for the cast.

Accordingly, one of the most important features of the present invention is its universal application and adjustability. The suspensory strap utilizes Velcro material for securing the strap. Metal loops stitched to tabs provide the adjustable feature when the Velcro material is placed in the tab loop, looped back upon itself and secured. The tabs are designed for the various applications for which the suspensory strap is utilized. Longer tabs are used with splints having a Velcro exterior. Shorter tabs are used for inserting embedding into the cast for walking casts, cylindrical leg casts, amputation casts, and leg cast braces.

Another important feature of the present invention is the unique arrangement of the removable position strap which positions the suspensory strap from the user's shoulder in such a manner that the strap is comfortable and yet, does not slide off of the shoulder. The positioning strap is adjustable in the same manner as the suspensory strap is adjustable.

The suspensory strap includes a resilient portion which flexes as the user walks or moves; thus, providing support, yet making the use of the strap comfortable and allowing freer movement. The suspensory strap also provides a non-Velcro non-resilient portion which rests upon the shoulder to provide a comfortable weight-bearing surface.

Thus, these features and objects are attained according to the present invention by providing a novel over-the-shoulder suspensory support device for use with leg casts, leg splints and amputation casts. The device is comfortable, resilient, adjustable, universal in its applicability, provides a removable positioning strap with co-acting tab for adjustability. The invention also provides co-acting tabs for embedding in plaster casts, co-acting tabs for use with splints, ambulatory casts, amputation casts and leg braces. The present invention also provides a method for using the over-the-shoulder suspensory support device.

BRIEF DESCRIPTION OF THE DRAWINGS

The advantages of this invention will become apparent upon consideration of the following details of the invention, especially when taken in conjunction with the accompanying drawings wherein FIG. 1 is a fragmentary perspective view of the instant invention;

FIG. 2 is a view of a patient employing the instant invention from a quartering front view;

FIG. 3 is a view of a patient employing the instant invention from a quartering rear view;

FIG. 4 is a plan form view of the shoulder strap showing the materials used in its construction;

FIG. 5 is a fragmentary perspective view of the terminal end of the shoulder strap, including a view of a co-acting tab;

FIG. 6 is a fragmentary view of the terminal end of the positioning strap and co-acting tab;

FIG. 7 is a view of a patient employing the instant invention as adapted for use with an amputation cast;

FIG. 8 is a partial view of a patient's leg with an immobilizing splint in which a partial view of the shoulder strap and co-acting tab is shown.

DESCRIPTION OF THE PREFERRED EMBODIMENT

The invention is generally depicted at 10 in FIG. 1. The invention provides a shoulder strap 30 and a position strap 20. Shoulder strap 30 is also shown in FIG. 4 and is generally a flat elongated strip of material. Shoulder strap 30 could be made of any material and it is contemplated that it is not necessary that it be flat in all cases, but only that it have sufficient strength to support the cast or splint. In the preferred embodiment, shoulder strap 30 is made in nine (9) segments of material which are sewn together end to end. The terminal ends 31 and 32 of shoulder strap 30 are made of the hook-like Velcro material. Intermediate sections 38 and 39 are made of the loop-like Velcro material. Resilient sections 37 and 41 are made of a resilient or elastic material. Positioning strap securing portions 33 and 34 are made of Velcro loop-like material and weight bearing portion 36 is made of flat webbing.

Referring to FIG. 1, where it can be seen that invention 10 also includes positioning strap 20. Positioning strap 20 is an elongate flat strap used for positioning shoulder strap in a comfortable location so that shoulder strap 30 does not slide off the user's shoulder. Shoulder strap 20 is made of three (3) sections as can be seen in FIG. 1 and FIG. 5. End sections 26 and 24 are made of hook-like Velcro material and section 21 is made of loop-like Velcro material.

Also included in the invention are securing tabs 51 and 52 which are made of hook-like Velcro material doubled back on itself and stitched to secure metallic loop 53 and 54.

It is contemplated that for certain applications where it is necessary to have the tabs co-act with loop-like Velcro material at different positions that the tab be of a different length than that shown in FIG. 1. FIG. 8 shows an application where tab 56 is positioned next to Velcro material splint 63.

The use of the apparatus 10 will now be described. FIGS. 2, 3 and 7 depict a proper use of the invention 10. In FIG. 2, it can be shown that tab 52 is imbedded in cylindrical cast 61. The tab 52 is imbedded in the cast 61 when the cast is formed. At the same time, tab 51 is imbedded in the cast on the back side of the cast, as shown in FIG. 3. After cast 61 is in place and tabs 51 and 52 are imbedded, then shoulder strap 30 is placed over the shoulder of user 60. Although FIGS. 2 and 3 depict apparatus 10 supported from the right shoulder, the universal nature of the invention allows use with either shoulder, depending upon which leg the cast or splint is located. It is important that the shoulder strap 30 not cross shoulders, but depend directly from right shoulder to right leg or from left shoulder to left leg as is appropriate.

Once shoulder strap 30 is placed over the user's correct shoulder and positioned so that weight-bearing webbing 36 is in a comfortable position, then terminal ends 31 and 32 are looped through metallic loops 53 and 54 and adjusted for proper tension, then pressed against loop leg materials 38 and 39 to secure the shoulder strap 30 with the proper tension.

Once shoulder 30 is in place, the positioning strap 20 is attached, first by applying hook-like tab 26 to loop material portion 33 on the back of the user, as shown in FIGS. 1 and 3. Positioning strap 20 is then placed in position under user's arm opposite the side that the cast is worn and looped through metallic loop 23 of tab 22. Hook-like Velcro portion 24 is then threaded through metallic loop 23 and pressed against loop-like material 21 in the preliminary positioning. Positioning strap 20 is then adjusted up and down along strips 33 and 34, so that strap 20 is comfortably under the arm of user 60 and is neither too low nor too high, and does not chafe the user's chest or arm pit. When positioning strap 20 is in place in a comfortable position, then end 24 is adjusted along material 21, so that shoulder strap 30 is held in position in a comfortable manner.

As shown in FIG. 6, tabs which can be imbedded in the plaster can also be used for other applications, such as splints and the like. If it is necessary to change either the hook-like Velcro material to a loop-like material or vice versa, that change is well within the scope of this invention. In FIG. 6, tab 51 is shown in reversed relationship to that of tab 51 in FIG. 1. Loop-like material 56 can then be inserted to the inside of any loop-like Velcro material, if that particular application requires.

The universal nature of invention 10 can be shown in FIGS. 7 and 8. In FIG. 7, user 60 is fitted with an amputation stump 62 made of plaster-like material. Tabs 51 and 52 are imbedded in the plaster when the cast is formed, leaving metallic loops 53 and 54 exposed to co-act with shoulder strap 30. Positioning strap 20 is used in the manner previously described.

In FIG. 8, user 60 is depicted having an immobilizing splint 63 which is placed around the knee in many cases after cast 61 as shown in FIGS. 2 and 3 is removed. Immobilizing splint 63 provided with co-acting Velcro-like material can be supported by device 10 by use of co-acting tabs 56 attached to shoulder strap 30 as previously described.

Although specific materials, components, and method steps have been stated in the above description of the preferred embodiments of the invention, other suitable materials, porportions and steps may be used with satisfactory results. In addition, it will be understood that various other changes of the details, materials, steps, arrangements of parts and uses which have been herein described and illustrated in order to explain the nature of the invention will occur and may be made by those skilled in the art upon a reading of this disclosure, and such changes are intended to be included within the principles and scope of this invention as claimed.

I claim:

1. In combination with a leg cast, splint and the like, fitted onto a patient, the invention comprising, an elongated shoulder strap having a first end, a second end, and a mid-point, means for attaching said first end of the shoulder strap to the cast, and means for attaching said second end of the shoulder strap to the cast, said shoulder strap being draped over that shoulder which is on the same side of the patient as the leg onto which the cast is fitted whereby said first and second ends are suspended in substantially vertically upright relation from that portion adjacent the mid-point which engages the patient's shoulder, an elongated positioning strap having a front end and a back end wherein said front end of the positioning strap is attached to the shoulder strap between said first end of the shoulder strap and said mid-point of the shoulder strap and wherein said back end of the positioning strap is attached to the shoulder strap between said second end of the shoulder strap and said mid-point of the shoulder strap, said positioning strap extending from said shoulder strap, around that side of the patient's torso which is opposite the leg onto which the cast is fitted, and back to the shoulder strap, means for generally infinitely adjusting the length of the positioning strap within a finite range whereby said positioning strap is readily adjustable to fit patients of various sizes, means for generally infinitely adjusting the length of the shoulder strap within another finite range whereby said shoulder strap is readily precisely fitted to different types of casts on patients of various heights, said means for attaching said first and second ends of the shoulder strap to the cast comprising cast embedded tabs having a loop and wherein the first and second ends of the shoulder straps are comprised of a length of material co-acting in a loop with a length of the shoulder strap to removably secure said length of material to the length of shoulder strap and wherein the described strap loop is positioned through said tab loop.

2. The combination of claim 1 wherein a portion of the length of said shoulder strap is resilient.

3. The combination of claim 1 further comprising means for removably attaching said positioning strap to said shoulder strap.

* * * * *